United States Patent [19]

Kennedy

[11] Patent Number: 4,942,204
[45] Date of Patent: Jul. 17, 1990

[54] AMPHIPHILIC NETWORKS

[75] Inventor: Joseph P. Kennedy, Akron, Ohio

[73] Assignee: The University of Akron, Akron, Ohio

[21] Appl. No.: 232,444

[22] Filed: Aug. 15, 1988

[51] Int. Cl.$^5$ ............................................ C08F 255/08
[52] U.S. Cl. .................................... 525/293; 525/309; 525/910; 525/279; 525/296; 525/303
[58] Field of Search ................................ 525/293, 309

[56] References Cited

U.S. PATENT DOCUMENTS

| | | | |
|---|---|---|---|
| 4,085,168 | 4/1978 | Milkovich et al. ................ | 525/293 |
| 4,486,572 | 12/1984 | Kennedy ............................ | 525/283 |
| 4,613,652 | 9/1986 | Nakayama et al. ................ | 525/293 |

*Primary Examiner*—Wilbert J. Briggs, Sr.
*Attorney, Agent, or Firm*—Oldham & Oldham Co.

[57] ABSTRACT

New amphiphilic networks have been synthesized by free-radical copolymerization of hydrophobic methacryloyl capped polyisobutylenes (MA-PIB-MA) with hydrophilic 2-(dimethylamino)ethyl methacrylate (DMAEMA). Two MA-PIB-MAs have been prepared with $M_n=4920$ and 10,200, and two series of networks were prepared with MA-PIB-MA contents between 48% and 71.5%. Variation of the molecular weight of MA-PIB-MA and its concentration in the network allows for a wide range of mechanical properties and swellability in hydrophilic and hydrophobic solvents. Differential scanning calorimetry shows the existence of two glass transitions in these networks and thus indicates a phase-separated domain structure. Tensile strengths and elongations are dependent on MA-PIB-MA contents, varying from 57.7 kg/cm$^2$ to 39.8 kg/cm$_2$ and 168% to 200%, respectively, with increasing MA-PIB-MA content. Solvent swelling of the networks range from 170% to 20% in water and from 40% to 170% in n-heptane with increasing MA-PIB-MA contents.

9 Claims, 5 Drawing Sheets

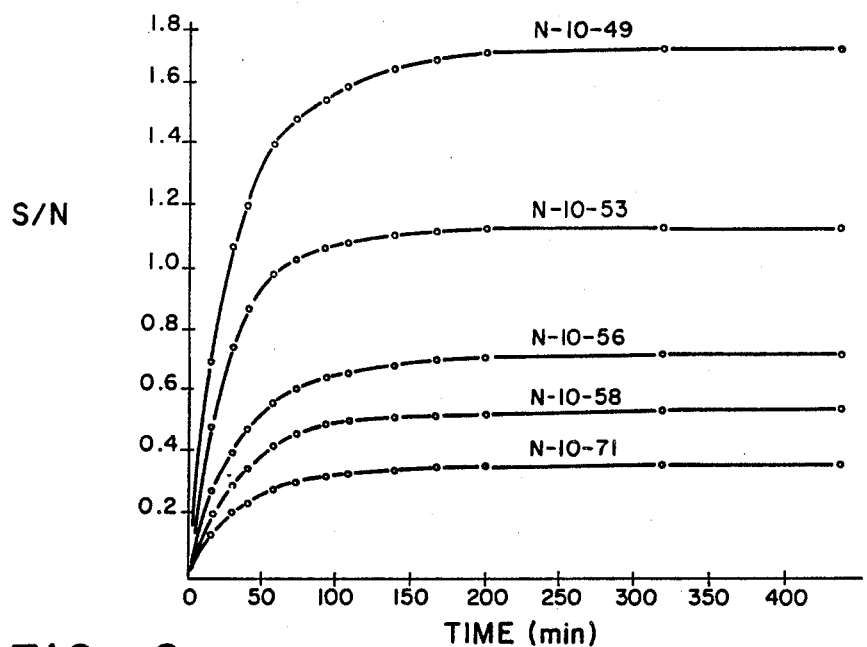
FIG.-6
FIG.-7
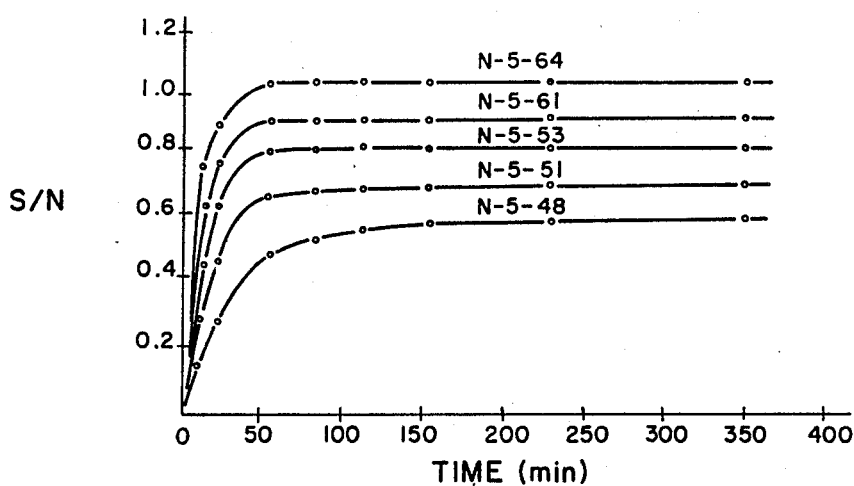

AMPHIPHILIC NETWORKS

This invention was made in the course of research which was supported by National Science Foundation (NSF) Grant DMR-84-18617.

TECHNICAL FIELD

This invention relates to amphiphilic polymer networks having hydrophobic polyolefin segments and hydrophilic segments, and to a method to preparing the same. More particularly, this invention relates to amphiphilic polymer networks in which mechanical properties and swellability in hydrophilic and hydrophobic solvents can be varied over a wide range by variation of the relative amounts of hydrophobic monomer portion and hydrophilic monomer portion.

BACKGROUND ART

An amphiphilic polymer network is a random assemblage of hydrophilic and hydrophobic polymer chains that is able to swell in both hydrophilic solvents (e.g., water) and hydrophobic solvents (e.g., a liquid hydrocarbon). Amphiphilic polymer networks are described, for example, in U.S. Pat. No. 4,486,572 to Kennedy (one of the applicants herein), and in Keszler and Kennedy, *Journal of Macromolecular Science*, Chemistry Edition, Vol. A21, No. 3, pages 319-334 (1984).

U.S. Pat. No. 4,085,168 to Milkovich et al. describes chemically joined, phase-separated self-cured hydrophilic thermoplastic graft copolymers which are copolymers of at least one hydrophilic (water soluble) ethylenically unsaturated monomer or mixture thereof and at least one copolymerizable hydrophobic macromolecular monomer having an end group which is copolymerizable with the hydrophilic monomer. The resulting copolymer is a graft copolymer characterized as having a comb-type structure consisting of a hydrophilic backbone polymer with hydrophobic polymer side chains bonded thereto. The side chains are disclosed as being bonded to the hydrophilic polymer at only one end of the side chain, so that no network results.

DISCLOSURE OF THE INVENTION

This invention according to one aspect provides a novel amphiphilic copolymer network comprising a free radical polymer product of (a) a hydrophobic bifunctional acryloyl or methacryloyl-capped polyolefin or mixture thereof, and (b) a hydrophilic, monofunctional comonomer.

The network is in the form of hydrophilic polymer chains and hydrophobic polymer side chains which cross-link the hydrophilic chains. The amphiphilic network has two glass transition temperatures indicating a phase-separated domain structure, and is swellable but insoluble in both water and n-heptane. These amphiphilic networks have various biomedical applications.

This invention according to another aspect provides a process for preparing an amphiphilic polymer network as described above, wherein a (meth)acryloyl-capped polyolefin is copolymerized with a dialkyl aminoalkyl (meth)acrylate under free radical polymerization conditions.

BRIEF DESCRIPTION OF THE DRAWING

In the drawings:

FIGS. 5 and 6 are swelling curves of representative of amphiphilic networks of this invention in water at room temperature.

FIGS. 7 and 8 are swelling curves of representative amphiphilic networks of this invention in n-heptane at room temperature.

BEST MODE FOR CARRYING OUT THE INVENTION

Figure 1:
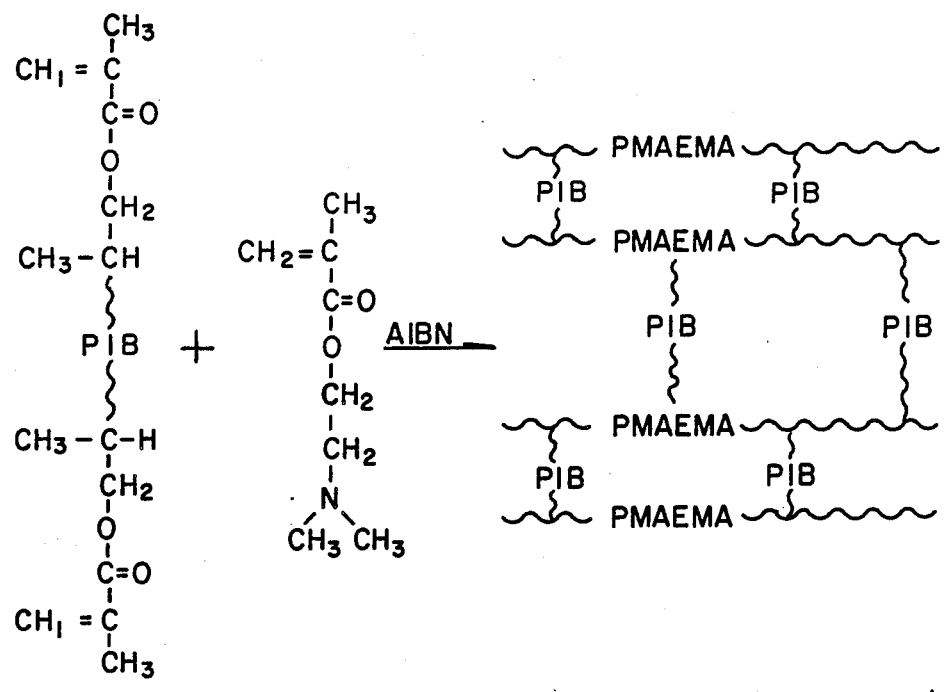
FIG. 1 is a schematic representation of a preferred amphiphilic polymer network of this invention and the reaction involved in its synthesis.

This invention will be described with particular reference to synthesis of amphiphilic networks from methacryloyl-capped polyisobutylene (the hydrophobic macromolecular monomer) and 2-dimethylaminoethyl methacrylate, which constitutes the best mode and preferred embodiment of this invention.

Starting materials for preparation of amphiphilic networks of this invention are (a) a hydrophobic acryloyl or methacryloyl-capped polyolefin and (b) a hydrophilic omega (di-alkylamino) lower alkylacrylate or methacrylate.

The hydrophobic methacryloyl-capped polyolefin is a bifunctional macromolecular monomer, or more simply a macromonomer which may be represented by the following formula (I)

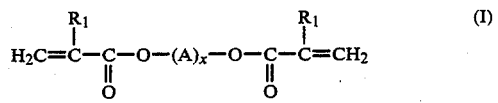

wherein:

A is a divalent unit derived from an olefin having four to about twelve carbon atoms or a mixture thereof, and $R_1$ is hydrogen or methyl, and x is the degree of polymerization of the macromonomer represented by formula (I).

The macromer (I) is a linear polyolefin having a number average molecular weight $M_n$ of at least about 2,000, preferably from about 2,000 to about 50,000, more preferably from about 4,000 to about 12,000, a degree of polymerization x corresponding to this $M_n$ (i.e, x is from about 35 to about 100), and a molecular weight distribution $M_w/M_n$ from about 3.0 to about 1.1, and capped at both ends with acryloyl or methacryloyl groups. Synthesis of the preferred macromonomer (I), i.e., methacryloyl-capped polyisobutylene is described in J. P. Kennedy and M. Hiza, *Polymer Bulletin*, Vol. 10, pages 146-151 (1983). Other macromonomers of the formula (I) may be prepared by an analogous method, substituting acrylate for methacrylate ester and/or substituting another olefin having 4 to 12 carbon atoms, preferably another alpha mono-olefin such as 1-butene, 3-methyl-1-butene, styrene, etc., for isobutylene.

The hydrophilic comonomer is a monofunctional compound or mixture thereof that is copolymerizable with the acryloyl or methacryloyl end groups of the hydrophobic acryloyl or methacryloyl capped polyolefin and which yields a water soluble segment when homopolymerized. Preferred hydrophilic comonomers are aminoalkyl acrylates and methacrylates of the following formula (II):

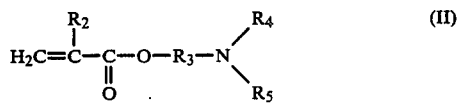

wherein:

$R_2$ is hydrogen or methyl, $R_3$ is an alkylene group of 2 to about 4 carbon atoms, and $R_4$ and $R_5$ may be the same or different and each is hydrogen or an alkyl radical of 1 to about 4 carbon atoms.

The preferred (meth)acrylate ester reactant of the formula (II) is 2-(dimethylamino)ethyl methacrylate.

Other suitable hydrophilic comonomers include N-vinyl pyrrolidone, acrylamide and 2-hydroxyethyl methacrylate (HEMA).

Preferably the hydrophobic macromer (I) and the hydrophilic comonomer have the same ester group, which is preferably methacryloyl, so that the amphiphilic polymer network which is formed will be a random copolymer.

The weight ratio of hydrophobic macromer to hydrophilic comonomer is generally in the range of about 80:20 to about 20:80, preferably about 70:30 to about 30:70, most preferably from about 60:40 to about 40:60.

Copolymerization of the hydrophobic macromonomer with the hydrophilic comonomer is carried out under conventional free radical polymerization conditions, in a suitable organic solvent such as tetrahydrofuran, methylene chloride, beuzeue, or heptane, at a temperature from about 40° to about 90° C., for a time sufficient to achieve the desired degree of cross-linking and to consume most of at least one of the two monomers (typically about 3 days at 60° C. will achieve the desired copolymerization), in the presence of a free radical initiator such as azobis(isobutylronitrile) (AIBN), cumyl peroxide or tert.-butylhydroperoxide. This reaction is shown in FIG. 1, which gives the preferred reactants, i.e., methacryloyl-capped polyisobutylene (MA-PIB-MA) (formula I-a) and dimethylaminoethyl methacrylate (DMAEMA) (formula II-a) and the preferred initiator (AIBN) by way of example.

Figure 1A:
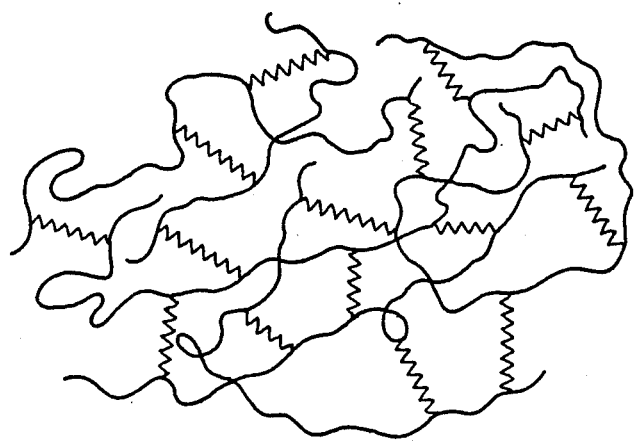
FIG. 1A is a further schematic representation of an amphiphilic polymer netowrk of this invention.

When the reaction is complete, the reaction product may be cooled to ambient temperature and may be extracted sequentially with a non-polar organic solvent (e.g., n-hexane), a polar organic solvent (e.g., ethanol) and water, to remove unreacted hydrophobic macromer (e.g., MA-PIB-MA), unreacted hydrophilic comonomer (e.g., DMAEMA) and hydrophilic homopolymer (e.g., poly(dimethylaminoethyl)methacrylate homopolymer), which may be represented either as PDMAEMA or PMAEMA. This leaves an amphiphilic polymer network according to the invention. This amphiphilic polymer network is shown schematically in FIGS. 1 and 1A. This network consists of hydrophilic chains (of PMAEMA, for example) which are connected to hydrophobic chains (e.g., of MA-PIB-MA) which constitute the cross-linking agent, at trifunctional cross-link points. In FIG. 1A, the hydrophilic chains are represented by smooth curved lines and the hydrophobic chains are represented by wavy lines. As may be seen in FIG. 1A, the hydrophilic polymer chains are for the most part linear although some branching does occur.

Amphiphilic polymer networks of this invention may have hydrophobic macromer contents ranging from about 40 to about 80% by weight, preferably from about 45 to about 75% by weight, based on total polymer content (which is the sum of hydrophobic macromer and hydrophilic polymerized acrylate or methacrylate). The preferred amphiphilic polymer network consists essentially of about 40 to about 80% by weight, preferably about 45 to about 75% by weight of MA-PIB-MA, balance poly[2-(dimethylaminoethyl) methacrylate] (PDMAEMA or PMAEMA), the latter being the hydrophilic component and the former being the hydrophobic component. Differential scanning calorimetry (DSC) shows the existence of two glass transition temperatures in these networks, indicating a phase-separated domain structure.

The average molecular chain length $\overline{M}_c$ of the hydrophilic polymer chain (i.e., PDMAEMA) between two crosslink sites may vary over a wide range, from about 1,000 up, typically from about 1,200 to about 6,000, depending on the weight percentage of hydrophobic macromer units (i.e., MA-PIB-MA) in the network and the number average molecular weight $\overline{M}_n$ of these macromer units. The $\overline{M}_c$ of hydrophilic chain increases with increasing $\overline{M}_n$ value of the hydrophobic macromer and with decreasing weight ratio of hydrophobic macromer to hydrophilic monomer in the reactant charge. The $\overline{M}_c$ values for hydrophilic polymer chain herein are calculated on the assumption that all of the hydrophobic macromer is incorporated into the amphiphilic polymer network, an assumption which is not always correct, particularly at higher hydrophobic macromer/hydrophilic monomer charge weight ratios. The average molecular chain length, or $\overline{M}_c$, value for the hydrophobic macromer is assumed to be the same as the $\overline{M}_n$ value of the hydrophobic macromer.

Amphiphilic polymer networks of this invention are swellable in both water (and other polar solvents) and in n-heptane (and other non-polar solvents), but are not soluble in either. Solvent swelling of the preferred networks (MA-PIB-MA/PDMAEMA) ranges from about 170% to about 20% in water and from about 40% to about 170% in n-heptane with increasing MA-PIB-MA content. (The maxima and minima indicate the percentage swelling in networks containing 48% and 71.5%, respectively of MA-PIB-MA). Networks according to this invention in which the hydrophobic macromonomer is based on an olefin other than isobutylene, and/or in which the hydrophilic polymer chains are based on a monomer other than DMAEMA, exhibit about the same swellability in both water and n-heptane as do the preferred amphiphilic polymer networks.

Tensile strength and elongation in amphiphilic networks of this invention are controllable. Tensile strength typically varies from about 35 to about 60 kg/cm² to about 60 kg/cm² and elongation typically varies from about 160% to about 210%, the former decreasing and the latter increasing with increasing hydrophobic macromer content. By way of illustration, the preferred MA-PIB-MA/DMAEMA networks exhibited tensile strength varying from 57.7 kg/cm² to 39.8 kg/cm² (at MA-PIB-MA contents of 48% and 71.5%, respectively) and elongations of 168 to 200%

(also at MA-PIB-MA contents of 48 and 71.5%, respectively).

The amphiphilic polymer networks of this invention are hydrogels which in the hydrated state are structurally similar to natural tissue. As a result, these materials find use for various biomedical applications. These networks may be used for controlled drug release devices, implants for enzyme immobilization, artificial arteries, blood-contacting applications various implantable reservoirs for drugs and metablites for veterinary and human applications. For biomedical applications the preferred hydrophobic macromonomer content (e.g., MA-PIB-MA) is from about 53 to about 58% by weight, based on total polymer weight.

Networks of this invention can be cast into thin films, and may also be cast into desired shapes.

Throughout this specification and claims, all percentages are by weight and are based on total amphiphilic polymer network weight unless otherwise stated.

This invention will now be described in further detail with reference to the specific examples which follow.

EXAMPLES 1-10

Materials

Methacryloyl capped polyisobutylene (MA-PIB-MA) was synthesized according to the procedure described in J. P. Kennedy and M. Hiza, *Polymer Bulletin*, Vol. 10, page 146 (1983). Two batches, having number average molecular weights $\overline{M}_n$ of 4,920 and 10,200, respectively, were prepared. These two macromers are designated as N-5 and N-10, respectively, hereinafter. Molecular characteristics of these macromers are shown in Table I. 2-(Dimethyamino)ethyl methacrylate was used without further purification. Isobutyronitrile) (AIBN) was recrystaleized from methanol. Tetrahydrofuran (THF) was distilled over calcium hydride. n-Heptane (reagent grade) was used without further purification.

Network Synthesis

Amphiphilic polymer networks were prepared in film and cube shapes. In the case of film, the copolymerization of MA-PIB-MA with DMEAMA was carried out in one ounce cylindrical bottles using AIBN initiator and THF solvent at 60° C. Before the system jelled and became unpourable the mixture was transferred to an aluminum dish, which was then placed in an oven protected with a nitrogen atmosphere at 60° C. for three days to give a film with a thickness of about 1 mm. It is important to avoid transferring the reactant mixture from the cylindrical bottle to the aluminum dish too soon, since early transfer will result in phase separation during film formation. One can determine a suitable time for transfer by running at least two samples of each composition, noting from the first the length of time for gelation to occur, and then transferring the second sample to the aluminum dish just short of that time. In the case of the cube, the polymerization charge was kept in the cylindrical bottle for three days and was then cut into cubes having sides approximately 6 mm.

To remove unreacted MA-PIB-MA, unreacted DMAEMA, and PDMAEMA homopolymer, the network was extracted sequentially with n-hexane for 24 hours, ethanol for five hours, and water for two days, all at room temperature (about 20°-25° C.).

Swelling

Swelling experiments were carried out by the use of both distilled water and n-heptane. The dried and weighed network was placed in solvent (water or n-heptane) and was then weighed periodically until a constant weight was reached. Swelling experiments were carried out at ambient temperature. The swelling curve was obtained by plotting the amount of solvent-absorbed per gram of network (S/N) against time.

Analytical Techniques

Molecular weights ($\overline{M}_n$ and $\overline{M}_w$) of the two MA-PIB-MA macromers were determined by a Waters Associates high pressure GPC instrument [Model 6,000 A Pump, WISP 710 B Automatic Injector, a series of five $\mu$-Styragel columns ($10^5$, $10^4$, $10^3$, 500 and 100 A), Differential Refractometer 2401, and UV Absorbance Detector 440].

Figure 2:
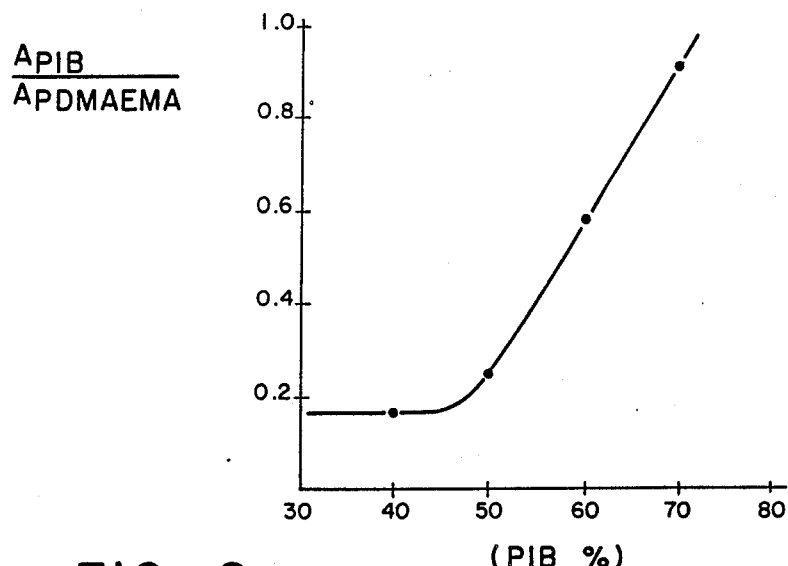
FIG. 2 is an FTIR calibration curve for preferred amphiphilic networks of the invention.

Number average terminal functionality $F_n$ of the MA-PIB-MA macromers was determined spectroscopically by nuclear magentic resonance (NMR) and by FTIR, the latter using a Beckman FT 2100 spectrometer equipped with a Spectra Tech Model 300 ATR (attenuated total reflectance) attachment. ATR spectra were drawn with a 50 mm KRS-5 crystal at a 45° angle. A doublet at 1362 and 1400 $cm^{-1}$, due to gem-$CH_3$ groups in MA-PIB-MA, was used to quantitate the MA-PIB-MA in the network. An absorption at 2772 $cm^{-1}$, due to $-CH_2-$ stretching vibration in a tertiary amine, was used to quantitate the PDMAEMA content in the network. Quantities thus obtained by analysis of the networks after extraction were compared with the FTIR calibration curve shown in FIG. 2. In FIG. 2, relative absorbances of PIB (polyisobutylene) and PDAEMA, or more precisely, the absorbance ratio $A_{PIB}$ and AP-DAEMA, respectively, as a function of weight percentage of PIB, is shown. This calibration curve was constructed by preparing a series of networks having different compositions and analyzing the MA-PIB-MA reactant of the unextracted networks (so that network, homopolymer and unreacted monomers are still present). Unextracted networks must be used to insure that the true overall amounts of MA-PIB-MA and DMAEMA charged are obtained for calibration purposes (since the FTIR absorptions of gem-$CH_3$ groups in MA-PIB-MA and of $-CH_2-$ in the tertiary amine should be the same in the network, homopolymer or unreacted monomer). As may be seen from the calibration curve in FIG. 2, sensitivity of this technique is very good at PIB contents over about 50%; however, below about 47% PIB in the network, sensitivity of this technique is unsatisfactory.

DSC analysis was carried out on a duPont 1090 Thermal Analayzer under nitrogen at a heating rate of 20%C/min.

Stress-strain data were obtained on an Instron Universal Testing Instrument with a 5 kg load cell and 5 cm/min cross-head speed at room temperature using microdumbbell samples.

Results

Network characteristics of 10 amphiphilic polymer networks, prepared with two different MA-PIB-MA samples having $\overline{M}_n$ values of 4920 and 10200, respectively, and prepared with different realtive amounts of MA-PIB-MA and DMAEMA in the reactor charge (i.e., the weight of reactants charged to the reactor), are shown in Table II below. The amount of PIB in each network was obtained by comparing the absorption ratio of PIB and of DMAEMA in the network (the unknown) vs. the relative absorbances in a mixture of known composition. In Table II, the network abbreviation code indicates an $\overline{M}_n$ of MA-PIB-MA macromonomer (rounded to the closest thousand and divided by 1000) and the percentage of PIB in the network. For example, N-5-48 indicates a network prepared with MA-PIB-MA having an $M_n=4920$ and containing 48.5% PIB. Also in Table II, the average chain length $M_c$ of PDMAEMA is calculated on the assumption that all of the MA-PIB-MA enters into the network. This is not always the case, especially at higher MA-PIB-MA/DMAEM charge ratios, as shown by the relative weight percentage of extracting materials (extract) and the fact that the PIB percentage at high MA-PIB-MA/DMAEMA charge ratios may be slightly lower in the network product than in the charge.

Figure 3:
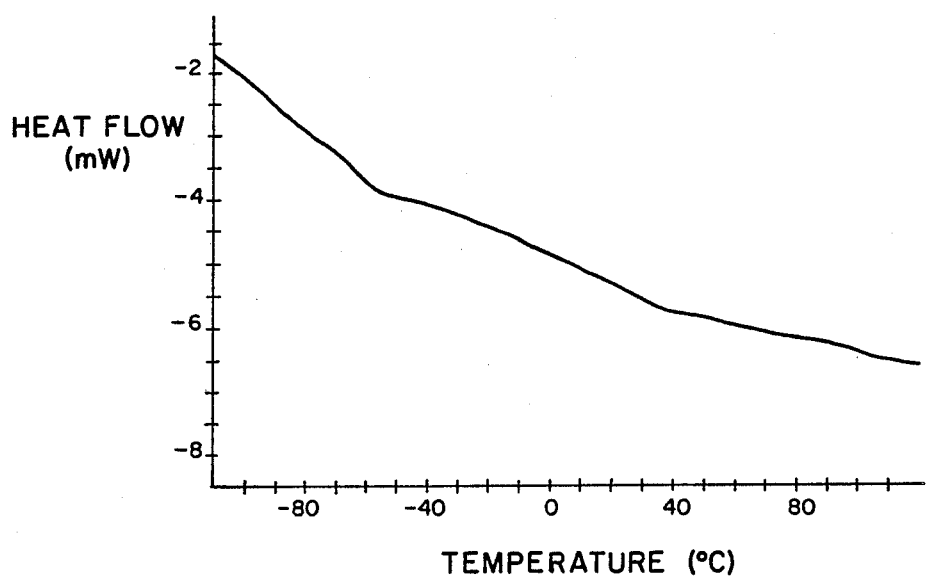
FIG. 3 is an DSC trace of a representative amphiphilic network prepared according to this invention.

The DSC trace of amphiphilic network N-10-56 (prepared in Example 8) is shown in FIG. 3 and given in Table III. This trace shows heat flow in miliwatts (mW) as a function of temperature. The negative signs denote heat outflow. The network exhibits two glass transition temperatures ($T_g$), one at $-60°$ C. and one at $30°$ C., indicating phase segregation into PIB ($T_g=-73°$) and PDMEMA ($T_g=19°$ C.) domains. The higher than literature $T_g$ values may be due to the relatively fast rate of heating used herein ($20°$ C./min) or to the restricted motion of the network chain segment.

Figure 4:
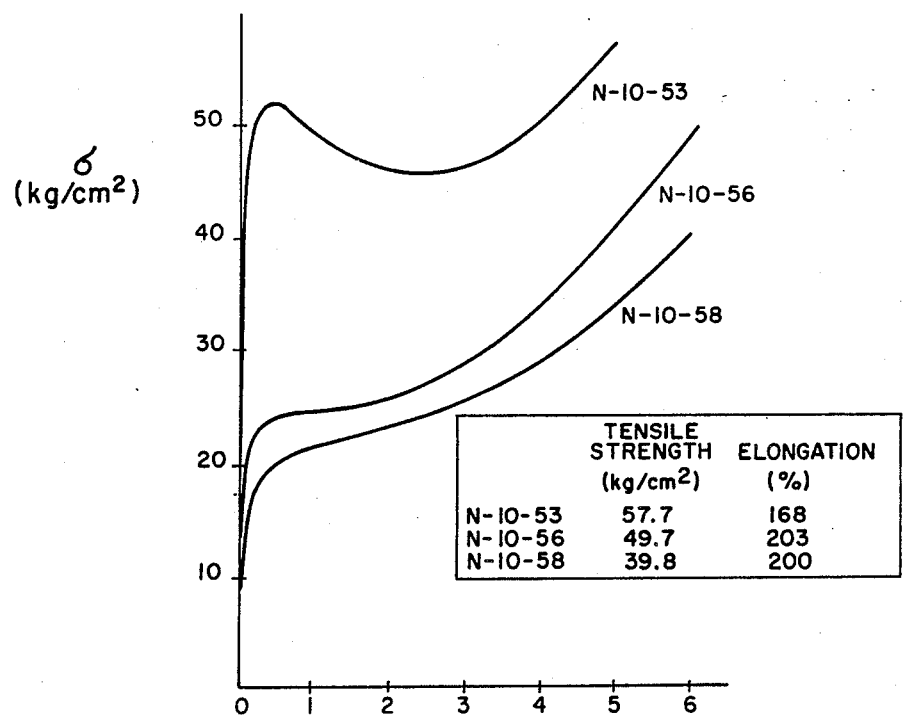
FIG. 4 is a series of stress/strain curves of amphiphilic networks of this invention.

Mechanical properties of three amphiphilic polymer networks (those of Example 7, 8 and 9) are given in Table IV and shown in FIG. 4. Table IV gives tensile strength (in kilograms per square centimeter) and percentage elongation (both at break) of these networks, while FIG. 4 shows the stress-strain curves of these networks. The networks were oven-dried at $60°$ C. under nitrogen atmosphere for 25 hours before the stress/strain curves were run. As is apparent from FIG. 4, network N-10-53 (Example 7) has a stress-strain curve with an essentially linear region of high modulus at low elongation, a yield point (at a stress of about 52 kg/cm² and an elongation of about 50%), and a non-linear region including a retrograde slope at higher elongations. The other two networks, having larger PIB contents, did not exhibit yield points. These curves show the tensile strength increases at percentage elongation at break decreases (generally) with increasing PDMAEMA content, although there was little difference in elongation at break between networks N-10-56 and N-10-58.

FIGS. 5-8 show the extent of swelling of amphiphilic networks of this invention in water and n-heptane. The degree of swelling, S/N, is shown as a function of time. The degree of swelling, S/N, represents the incremental volume (S) divided by the original volume (N) of the network before imbibation of water.

Figure 5:
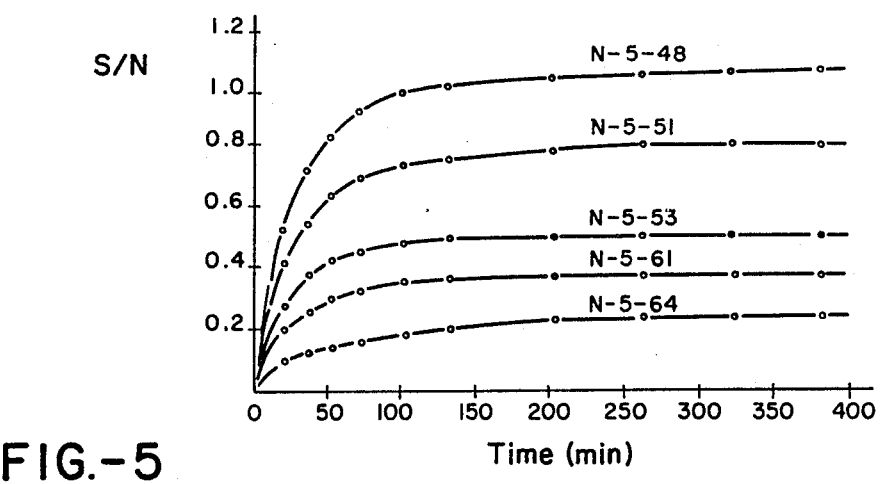

FIG. 5 show the extent of swelling of the amphiphilic networks of Examples 1-5 in water.

FIG. 6 show the swelling of the amphiphilic networks of Examples 6-10 in water.

Figure 8:
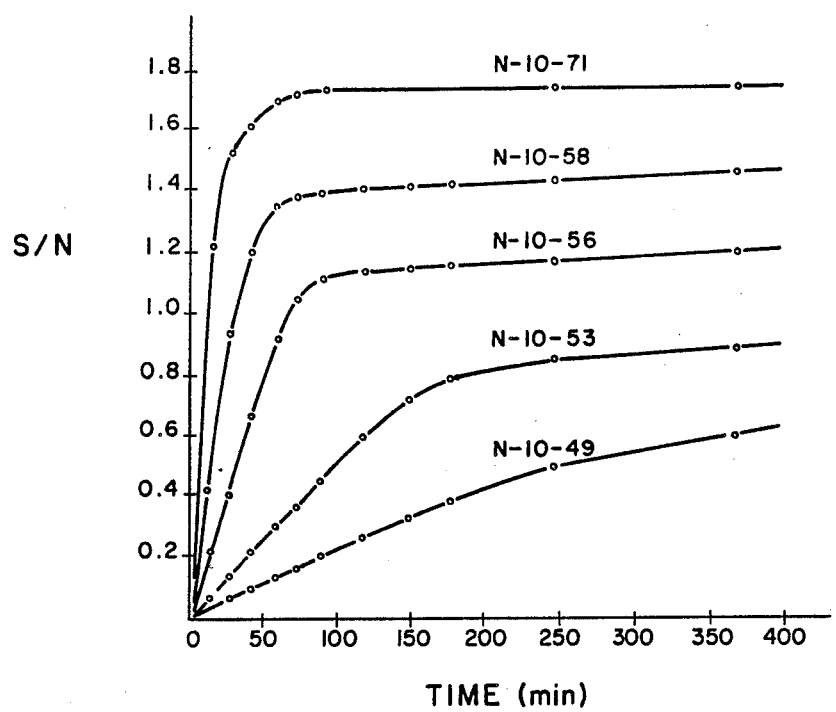

FIGS. 7 and 8, show swelling of amphiphilic networks in n-heptane at room temperature. Date for the amphiphilic networks of Examples 1-5 are given in FIG. 7; data for the networks of Examples 6-10 are given FIG. 8.

All of the amphiphilic networks exhibited an equilibrium degree of swelling, as shown by the fact that there is virtually no change in volume after 210 minutes. As the data in FIGS. 5-8 show, swelling in water decreases and swelling in n-heptane increases with increasing PIB content.

While this invention has been described with reference to specific embodiments thereof, it should be understood that these embodiments are by way of illustration and not limitation, and the scope of the invention shall be measured by the appended claims.

TABLE I

| | Molecular Characteristics of MA-PIB-MAs Used For Network Synthesis | | | |
|---|---|---|---|---|
| MA-PIB-MA | $\overline{M}_n$ | $\overline{M}_w/\overline{M}_n$ | NMR | $\overline{F}_n$* FTIR |
| N-5 | 4920 | 1.6 | 1.99 | 2.27 ± 0.2 |
| N-10 | 10200 | 1.7 | 2.0 | 2.0 ± 0.2 |

*Number average terminal functionality determined spectroscopically

TABLE II

Network Synthesis Conditions and Compositions
(Copolymerizations in 7 ml THF with 0.07 g AIBN at 60° C.)

| | | Charge | | | Network Characteristics | |
|---|---|---|---|---|---|---|
| | Network | MA-PIB-MA | DMAEMA | Extract | | |
| Example | abbrev. | (g) | (g) | (%) | PIB (%) | $M_c$, PDMAEMA* |
| 1 | N-5-48 | 0.6 | 1.4 | 21.4 | 48.5 | 2610 |
| 2 | N-5-51 | 0.8 | 1.2 | 26.5 | 51.0 | 2360 |
| 3 | N-5-53 | 1.0 | 1.0 | 27.1 | 53.0 | 2180 |
| 4 | N-5-61 | 1.2 | 0.8 | 29.3 | 61.0 | 1570 |
| 5 | N-5-64 | 1.4 | 0.6 | 30.5 | 64.0 | 1380 |
| 6 | N-10-49 | 0.6 | 1.4 | 20.7 | 49.5 | 5190 |
| 7 | N-10-53 | 0.8 | 1.2 | 22.4 | 53.0 | 4700 |
| 8 | N-10-56 | 1.0 | 1.0 | 23.8 | 56.3 | 3950 |
| 9 | N-10-58 | 1.2 | 0.8 | 27.3 | 58.2 | 3660 |
| 10 | N-10-71 | 1.4 | 0.6 | 35.7 | 71.5 | 2030 |

*Calculated; for assumptions see text

TABLE III

| DSC Trace of Amphiphilic Network N-10-56 (Example 8) | |
|---|---|
| Temp., °C. | Heat Flow, mW |
| −110 | −1.8 |
| −60 | −4.0 |
| +30 | −5.5 |
| +120 | −6.5 |

TABLE IV

Stress-Strain Curves of Amphiphilic Networks

| Example | Network | Tensile Strength (Kg/cm$^2$) | Elongation % |
|---|---|---|---|
| 7 | N-10-53 | 57.7 | 168 |
| 8 | N-10-56 | 49.7 | 203 |
| 9 | N-10-58 | 39.8 | 200 |

What is claimed is:

1. An amphiphilic copolymer network swellable in water or n-heptane but insoluble in either, composed of a polymeric product of reaction of an acrylate or methacrylsyr of dialkyl amino alkyl with a hydrophobic bifunctional acryloyl or methacryloyl capped polyolefin.

2. An amphiphilic network according to claim 1 characterized by ability to absorb, on a weight basis, about 20 to about 170% by weight of water and about 40 to about 170% by weight of n-heptane.

3. An amphiphilic network according to claim 1, said network having two glass transition temperatures.

4. An amphiphilic network according to claim 1 in which said polyolefin is a polymer of an olefin monomer containing from 4 to 10 carbon atoms.

5. An amphiphilic network according to claim 4 in which the olefin monomer is isobutylene.

6. The amphiphilic copolymer of claim 1 wherein the acrylate or methacrylate of dialkyl amino alkyl is 2-(dimethylamino) ethyl.

7. The amphiphilic copolymers of claim 1 wherein the hydrophobic bifunctional acryloyl or methacryloyl capped polyolefins has a molecular weight distribution $M_w/M_n$ from about 1.7 to 1.1.

8. An amphiphilic network according to claim 1 consisting essentially of a polymer product of (a) about 40 to about 75 percent by weight of a hydrophobic methacryloyl capped polyisobutylene and (b) about 25 to about 60 percent by weight of hydrophilic 2-(dimethylamino)ethyl methacrylate, based on total polymer weight.

9. An amphiphilic polymer network according to claim 1 said network consisting essentially of the product of (a) about 53 to about 58 percent by weight of said hydrophobic methacryloyl capped polyisobutylene and (b) about 42 to about 47 percent by weight of said hydrophilic 2-(dimethylamino)ethyl methacrylate, based on total polymer weight.

* * * * *